United States Patent
Massen et al.

[11] Patent Number: 5,372,502
[45] Date of Patent: Dec. 13, 1994

[54] OPTICAL PROBE AND METHOD FOR THE THREE-DIMENSIONAL SURVEYING OF TEETH

[75] Inventors: Robert Massen, Radolfzell; Joachim Gässler, Constance, both of Germany

[73] Assignee: Kaltenbach & Voight GmbH & Co., Germany

[21] Appl. No.: 788,832

[22] Filed: Nov. 7, 1991

Related U.S. Application Data

[63] Continuation-in-part of Ser. No. 397,113, Aug. 22, 1989, abandoned.

[30] Foreign Application Priority Data

Sep. 2, 1988 [DE] Germany .................... 3829925

[51] Int. Cl.$^5$ ............................... A61C 5/00
[52] U.S. Cl. ............................................ 433/215
[58] Field of Search ............... 433/215, 229, 214, 213; 356/376

[56] References Cited

U.S. PATENT DOCUMENTS

| | | | |
|---|---|---|---|
| 3,817,635 | 6/1974 | Kawahara | 356/171 |
| 4,443,706 | 4/1984 | DiMatteo et al. | 250/558 |
| 4,575,805 | 3/1986 | Moermann et al. | 364/474 |
| 4,594,001 | 6/1986 | DiMatteo et al. | 356/376 |
| 4,611,288 | 9/1986 | Duret et al. | 364/474 |
| 4,643,578 | 2/1987 | Stern | 356/376 |
| 4,742,464 | 5/1988 | Duret et al. | 364/474 |
| 4,825,263 | 4/1989 | Desjardins et al. | 356/376 |
| 4,837,732 | 6/1989 | Brandestini et al. | 364/413.28 |
| 4,952,149 | 8/1990 | Duret et al. | 433/215 |
| 4,964,770 | 10/1990 | Steinbichler et al. | 433/223 |
| 5,175,601 | 12/1992 | Fitts | 356/376 |

FOREIGN PATENT DOCUMENTS 0040165  11/1981  European Pat. Off. ............ 433/214

Primary Examiner—Gene Mancene
Assistant Examiner—Jeffrey A. Smith
Attorney, Agent, or Firm—Scully, Scott, Murphy & Presser

[57] ABSTRACT

An optical oral or mouth probe which is utilized for the three-dimensional measurement or surveying of teeth possesses a highly-resoluting two-dimensional point-by-point freely-programmable projection unit, which generates a digitalized projection pattern from a computer in accordance with a programmed mathematical or graphical method, deposits the pattern in an image storage and is then brought into display through addressing of an LCD matrix plate, and with the aid of a focusing optic is then projected onto the surface which is to be surveyed or measured.

21 Claims, 2 Drawing Sheets

OPTICAL PROBE AND METHOD FOR THE THREE-DIMENSIONAL SURVEYING OF TEETH

CROSS-REFERENCE TO RELATED APPLICATIONS

The present application is a continuation-in-part application of U.S. Ser. No. 397,113 filed on Aug. 22, 1989 entitled OPTICAL PROBE FOR THE THREE-DIMENSIONAL SURVEYING OF TEETH IN THE ORAL CAVITY and which is now abandoned.

BACKGROUND OF THE INVENTION

1. Field of the Invention

The present invention relates to an optical probe for the three-dimensional surveying or measuring of teeth in the oral cavity of a patient.

2. Discussion of the Prior Art

The direct optical three-dimensional surveying or measuring of teeth in the oral cavity of a patient facilitates the obtainment of the digital constructional data necessary for the computer-controlled manufacture of tooth replacements without having to make any impressions of the teeth. In the semi-automatic or fully-automatic numerical milling technology, three systems are currently known which utilize this particular technology, and are summarized as follows:

a) A French system which is employed by Hennson Internation of Vienne, France, and based on the work of a physician, Dr. Duret, operates with a laser-triangulation method for the point-by-point measurement of the distance between the surface of the tooth and the optical probe which is inserted into the oral cavity of the patient. Such types of distance probes are also known for their applications in the industrial measuring technology. They carry out either a point-by-point distance measurement or survey, or through the scanning by the laser along a line, are able to determine the relative height coordinates of the scanned object along a scanning line. Inasmuch as CCD-scanning line sensors are ordinarily employed as optical pick-ups or receivers, there are picked up point rasters of from 256 to 4,096 image points.

b) A Swiss system utilized by the company of BRAINS, Brandistini Instruments, Switzerland, designated by the description CEREC, operates in accordance with the light-section method which is likewise known from the industrial measuring technology. Hereby, a single line or dash of light or a parallel grid consisting of dashes or lines of light are projected onto the surface and observed under a parallax-angle with a two-dimensional camera. From the curvature of the lines of the light-section, they can be computed back to the relative height.

Also known is an improved variant of this method, in essence, the so-called phase-shift method. This method employs an interferometrically-produced light grid with sinusoidal brightness modulation in contrast with the binary light-sections. Through the pick-up or recording of the object at a plurality of positions for the phase location of this grid, there can be obtained in a significantly higher point density of height values and any disturbing influences, such as non-constant background brightness and fluctuating stripe or line contrast caused by localized fluctuations in reflection, which can be mathematically eliminated.

c) A method which, at this time, has been developed at the University of Minnesota by a physician, Dr. Dianne Recow, takes multiple photographic exposures of the tooth surface with the aid of a laryngoscopic probe so as to, after their development, scan them with the aid of a document scanner, and to digitalize them and then evaluate them in a computer through the application of methods which are known from the photogrammetry for stereo-evaluation.

All of the optical mouth or oral probes which have been employed up to the present are characterized In that, necessitated by their constructions, embody only one of these possible methods (laser-triangulation, or light-section, or phase-shift or stereo-distance measurement). However, all of these methods, each considered in itself, are subject to a series of individual advantages and disadvantages; as follows:

a) Laser method for the triangulation or the phase-shift method suffer considerably under the speckle formation which is caused by the coherent light. This leads to blurred height images and therefore to a considerably reduced resolution in the final image.

b) Light-section and phase-shift methods with a constant grid suffer problems with regard to ambiguities at larger jumps in height. Such jumps displace the light line or, in essence, the phase position of the sinusoidal grid by more than one grid constant. Consequently, it is then no longer possible to reconstruct the jump in height.

In U.S. Pat. No. 4,952,149 to Duret et al., it is disclosed that by projecting first a phase-shifted sequence of coarse sinusoidal grids, the depth ambiguity resulting from a unique grid period can be resolved. Both the phase shifting-process and the change between a coarse and a fine grid require some type of mechanical moving parts, such as a stepper motor for translating the grids, a rotating glass plate or similar moving mechanical part. Moving parts are not welcome in a delicate dental probe which is subject to heat treatment for sterilization. They reduce the life time of such a probe and significantly increase the cost of production.

A second important draw back in the Duret et al. disclosure is that the projected image is fixed by construction to grid patterns with different positions with these probes to project alternate patterns which are useful in optical three-dimensional measurements of teeth. These probes are not capable of providing the following:

a) projection of constant white light which allows a better inspection of the particular tooth on a video monitor without disturbing grid patterns;

b) the projection of colored light using a color which is complementary to the color of the gingiva and gives a better contrast between the tooth surface and the gingiva;

c) the projection of a sequence of coded binary stripes utilizing grey code is an alternative method to the phase shifting technology presently utilized in coarse measurements;

d) the projection of light patterns useful for calibrations of the probe such as small light circles, the distortion of those circles into ellipses allows one for example to recover the absolute position of the probe in the mouth of the patient without using separate calibration dies or artificial marks on the tooth surface; and e) the projection of a image of the occlusions of the opposite tooth which would allow one to visually judge the fitting of the surfaces of opposite tooth, the visual correlation utilizing a colored image of the opposite occlusion into the tooth under treatment allows the dentist to judge the fitting between the new dental replacement and the opposite occlusion surfaces.

The heretofore known optical three-dimensional mouth or oral probes determine the three-dimensional method which is to be employed in dependence upon the construction thereof. With the exception of a few adjustment or setting parameters, such as scanning frequency, phase displacement, focusing and enlargement they are no longer variable. Consequently, it is not possible, with the same probe, to employ a plurality of the complementary measuring or surveying methods, such as triangulation, light-section, phase-shift, stereophotogrammetry, as well as a series of further three-dimensional optical measuring variants which are known from the industrial measuring technology; for example, such as grey code-encoded light grids on the same object in order to be able to combine the advantages of all methods and to avoid their disadvantages.

SUMMARY OF THE INVENTION

The present invention is directed to an optical three-dimensional measuring probe for the surveying of the three-dimensional geometry of teeth in the oral cavity of a patient. The measuring probe includes a highly-resoluting two-dimensionally point-by-point freely-programmable projection unit, an image memory for storing a digitalized projection pattern, an image computer having a microprocessor for the pixel-wise control of the projection unit utilizing a digital pixel image stored in the image memory, the digital pixel image being projected through an endoscopic probe onto the tooth surface which is to be surveyed, a charge-coupled image sensor for converting a distorted image reflected off the tooth surface upon which said digital image is projected into a form suitable for processing by said microprocessor, and said microprocessor comprising a program which calculates a topographic representation of the teeth in the oral cavity based upon a comparison between said distorted image and said digital pixel image. The invention further comprises a video monitor for displaying a topographic representation of the teeth in the oral cavity of a patient.

The foregoing object is inventively achieved in that an optical oral or mouth probe which is utilized for the three-dimensional measurement or surveying of teeth possesses a highly-resoluting, two-dimensional point-by-point freely-programmable projection unit, which generates a freely-programmable light pattern previously computed in a computer, stored as a digitized pixel pattern in a digital image buffer such that the numbers stored at every pixel location in the image buffer directly control the light intensity of associated pixel in the matrix-light source. This computer generated image is then projected with the aid of a focusing optic onto the surface which is to be surveyed or measured. Inventively, as the projection unit comprises a video-monitor cathode ray projection tube or spatial light modulators. The spatial light modulators are available in the form of inexpensive LCD screens or LCD matrix plates which are available in miniature television sets or in lap top computers and allow themselves to be easily integrated into such a mouth probe as an electronically-controllable transparency.

BRIEF DESCRIPTION OF THE DRAWINGS

Reference may now be had to the following detailed description of an exemplary embodiment of an inventive mouth probe possessing an LCD-matrix plate as a programmable light source, taken in conjunction with the accompanying drawings; in which.

DESCRIPTION OF THE PREFERRED EMBODIMENTS

An optical three-dimensional measuring probe is utilized to generate a three-dimensional image of a single tooth or a group of teeth within the oral cavity of a patient. The measuring probe projects a particular pattern onto the single tooth or group of teeth which is/are to be surveyed. The particular pattern projected can be, for example, a series of parallel stripes. This projected pattern of stripes is distorted by the tooth or teeth which is/are to be measured due to variations in height. Basically, the pattern is distorted by the tooth or teeth which is/are to be measured in that the individual stripes fall on sections of the tooth which are of different height or fall on different teeth which are different height. The distorted pattern is reflected back towards the measuring probe which captures the distorted pattern and transmits it ultimately to a computer. Through a comparison between the undistorted pattern projected by the probe and the distorted pattern reflected from the specific area within the oral cavity, information with respect to the topography of the tooth or teeth is obtained. In order to preclude ambiguities in this topographical information and to increase the precision of the measurement, the surveying procedure is repeated a number of times whereby the pattern which is projected against the tooth or teeth is always varied. Accordingly, the distorted pattern which is captured by the measuring probe will also vary; however, each iteration provides refinement of the topography.

Figure 1:
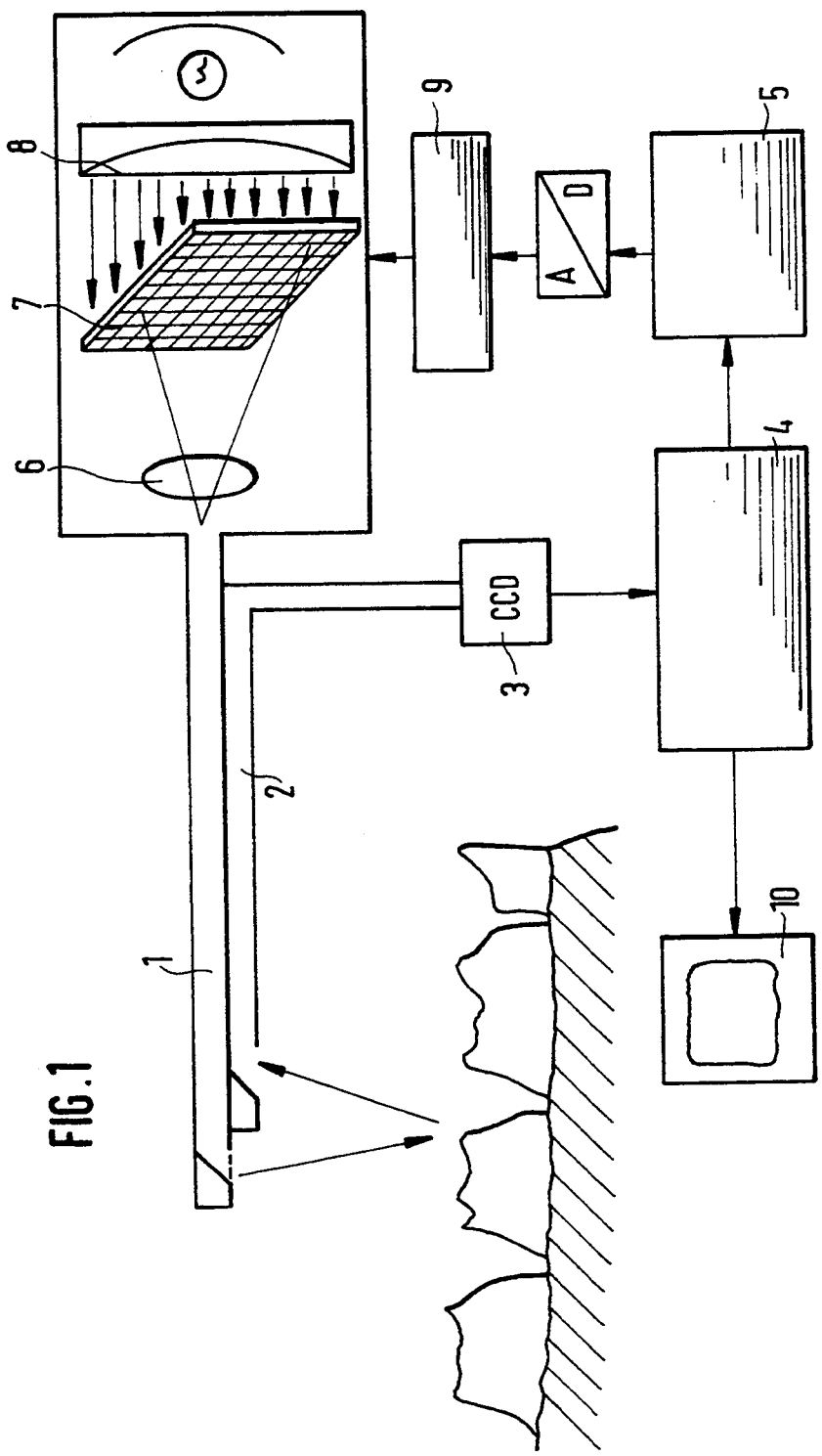
FIG. 1 illustrates a block diagram of the optical three-dimensional measuring probe of the present invention.

Referring to FIG. 1, there is shown a block diagram of the optical three-dimensional measuring probe. A highly-resoluting, two-dimensionally, point-by-point freely programmable projection unit 10 is utilized to generate the particular pattern which is to be projected onto the surface of the single tooth or group of teeth. The particular pattern or patterns which are to be projected are digitally generated by an image computer 12, whose operation is discussed in detail in subsequent paragraphs. The projection unit 10 comprises a point-shaped projection lamp 14, whose diverging light beams are focused into parallel light beams by a lens 16. The parallel light beams exiting the lens 16 are directed towards and incident upon a Liquid Crystal Display (LCD) matrix plate 18 which implements the particular projection pattern based on commands from the image computer 12. The operation of the LCD matrix plate 18 is also described in detail in subsequent paragraphs. The light pattern exiting the LCD matrix plate 18 is focused by a collector lens 20 and conducted by an endoscopic light conducting probe 22, which consists of a plurality of light conducting fibers, towards a first mirror 24. The first mirror 24 deflects or reflects the light pattern onto the specific area in the oral cavity, which is shown as a single tooth 26 in the figure.

The LCD matrix plate 18 is a typical liquid crystal display arranged in rows and columns which are addressed as discrete x and y positions. The LCD matrix plate can be a black and white liquid crystal display or a color liquid crystal display. Generally, these discrete x, y locations are referred to as picture elements or pixels. Through pixel addressing techniques accomplished by the image computer 12, various individual elements which comprise the LCD matrix plate 18 can be made transparent to light while other elements can be made impervious to light incident thereon. The particular arrangement of light transmitting and light blocking regions within the LCD matrix plate 18 determines the particular pattern which is projected onto the tooth 26, such as the aforementioned stripe pattern.

The addressing of the LCD matrix plate 18 is accomplished through the use of the image computer 12. The image computer 12 is a computer which contains a dedicated microprocessor which is preprogrammed to implement the various projection patterns such as the stripe pattern. The data or information used to generate the particular projection pattern is stored in a memory device 28. The data stored in the memory device 28 is a digitized pixel pattern. The data is a digitized pixel pattern stored in the memory device 28 in a manner such that the data stored at every pixel location in the memory device 28 directly controls the transmission or blocking of light in the LCD matrix plate 18. The memory device 28 can be any type of memory which is capable of storing digital data such as a RAM or ROM. The image computer 12 accesses the memory device 28 and outputs the address of the particular pixels necessary to implement the particular pattern to a computer interface unit 30. The computer interface unit 30 simply converts the digital signals from the image computer 12 into signals suitable for interaction with the LCD matrix plate 18.

The image or pattern projected onto the tooth 26 surface is reflected off the tooth and back towards the endoscopic probe 22. The reflected pattern, however, as mentioned before is a distorted version of the projected pattern. This distorted pattern is reflected off a second mirror 32 and into a second fiber optic path 34 within the endoscopic probe 22, which is similarly constituted of parallel light conducting fibers. By means of the light conducting fibers, the distorted pattern is conveyed to a charged-coupled image sensor 36 which is similar to a standard CCD array. The charged-coupled image sensor 36 is a device in which electrical charges are introduced when light from a scene is focused on the surface of the device 36. Basically, the distorted pattern, which is a light pattern, impinges upon the surface of the charge-coupled image sensor 36 and the sensor 36 sequentially accesses image points to produce a television type output signal. This television type output signal is in a digital format suitable for digital processing and is input into the image computer 12.

The image computer 12 then implements a software routine or program which takes the digital representation of the distorted signal output from the change-coupled image sensor 36 and compares it to the originally projected pattern to determine the topography of the tooth 26 based on the distortions due to height variations. The computed results are then displayed on a monitor 38 such as a standard CRT display.

Figure 2A:
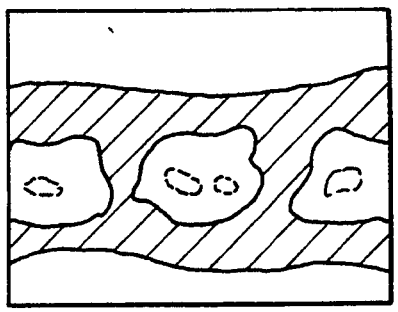
FIGS. 2a through 2e illustrate the use of a series of projection patterns as employed in a phase shift method of the present invention thereby resulting in an image without any ambiguities.
Figure 2B:
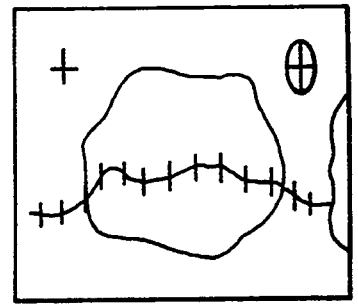
Figure 2C:
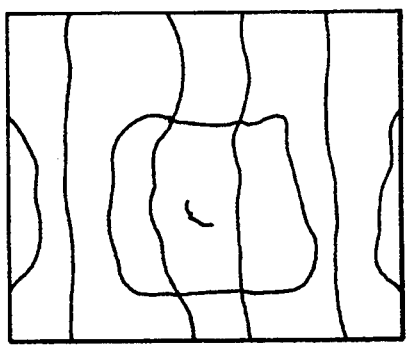
Figure 2D:
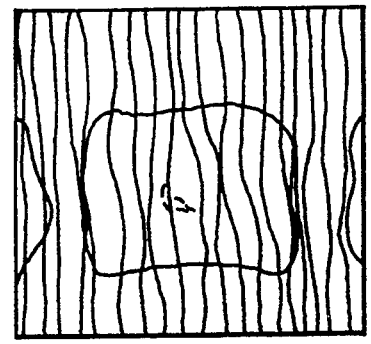
Figure 2E:
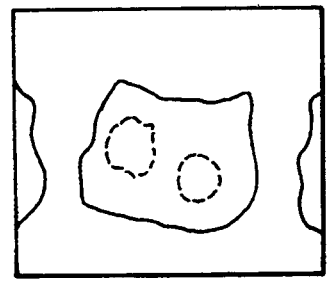

By way of example, FIGS. 2a through 2e of the drawings illustrate a series of projection patterns which cannot be produced with the usual probes without an exchange of the probe and/or without mechanical moving parts. In a first step, the projection pattern is projected "all white" as shown in the image or pattern of FIG. 2a. As a result thereof, the orientation of the probe, the setting of the sharpness and so forth, allow themselves to be easily controlled based on observations of the image displayed on the CRT monitor 38 of FIG. 1 without encountering any already disturbing stripes or lines. Moreover, zones of shade can be automatically recognized through a pure brightness evaluation, in which the subsequent three-dimensional surveying would become impossible or uncertain. A second projection pattern as shown in the image or pattern of FIG. 2b can be constituted, for example, from markings from whose distortion calibrating data can be computed (imaging condition, distance to a reference plane, and so forth). From the distortion of a circular marking into an ellipse there can be obtained the imaging relationships, the position in space of the background, and other data which are necessary for the calibrating of the entire optical system. For instance, the pattern shown in FIG. 2c is a rough sinus grid in order to implement a weakly-resoluting phase-shift method. This pattern is picked up or received in three different phase positions in order to facilitate the formation of a rough height image of the tooth. Due to the large grid constants, there are not encountered any ambiguities as in any of the other methods described. The pattern shown in FIG. 2d consists of a much finer sinus grid and facilitates a highly-resoluting height measurement, but always with encountered ambiguities. These ambiguities can be avoided with the results of the rough measurement of the pattern shown in FIG. 2c. The switching from a coarse to a fine grid protection can be as fast as the video frame rate of the charged-coupled image sensor 36, shown in FIG. 1, observing the scene. This is much faster then the known systems which use a mechanically moved grating. Speeding up the sequence of protection is important as both the probe and the patient must not move this process. The purely electronically operating LCD matrix plate 18 is therefore an improvement over the prior art and offers an advantage compared to previous rather slow solutions. Finally, it is possible, for example, to obtain a series of digitally stored tooth profiles from an image or pictorial library and to project these onto the tooth in order to be able to ascertain the quality thereof based purely on observations of the attached viewing or video monitor 38 shown in FIG. 1, and upon occasion, to select an already available tooth model. The details of the phase-shift method need not be repeated herein inasmuch as much as they correspond to the state-of-the-technology and have been sufficiently published. In the same manner, the other three dimensional surveying methods, such as triangulation method, photogrammetry, encoded projection pattern, and others are not elucidated any further since they have been published as the state-of-the-technology.

A further inventive concept resides in objecting a reference image in grey level or color, for example, of the stored picture or image of the occlusal surface of the oppositely located tooth, using the same LCD matrix plate in order to confirm the occlusion program. In the utilization of colored LCD video screens, such as are already commercially available, in addition to the three-dimensional surveying or measurement of the tooth which is to be treated, there can be concurrently obtained visual information by the treating dentist with respect to the occlusion problem.

This elucidated example illustrates the advantages and capabilities which are opened by an optical three-dimensional surveying probe with a freely-programmable projection pattern in comparison with the rigid and restricted capabilities of a grid pattern projection only which are currently afforded by known optical probes.

While the invention has been particularly shown and described with respect to preferred embodiments thereof, it will be understood by those skilled in the art that the foregoing and other changes in form and details may be made therein without departing from the spirit and scope of the invention, which should be limited only by the scope of the appended claims.

What is claimed is:

1. An optical three-dimensional measuring probe for the surveying of the three-dimensional geometry of teeth in the oral cavity of a patient, said probe including a highly-resolving two-dimensionally point-by-point freely-programmable projection unit, comprising a projection lamp for generating a plurality of light beams in a diverging pattern, an LCD matrix plate which translates said plurality of light beams into said pixel image for projection onto the tooth surface, lens means for focusing said diverging pattern of light beams into a plurality of parallel light beams passing through said LCD matrix plate to be translated into said pixel image, and collector lens means for directing said pixel image into a first fiber optic path within said endoscopic probe, through which said pixel image is projected onto the tooth surface, an image memory for storing a digitalized projection pattern, an image computer having a microprocessor for the pixel-wise control of said projection unit utilizing a digital pixel image stored in said image memory, said digital pixel image being projected through an endoscopic probe onto the tooth surface which is to be surveyed, a charge-coupled image sensor for converting a distorted image reflected off the tooth surface upon which said digital image is projected into a form suitable for processing by said microprocessor, said microprocessor comprising a program which calculates a topographic representation of the teeth in the oral cavity based upon a comparison between said distorted image and said digital pixel image, and a video monitor for displaying said topographic representation of the teeth in the oral cavity of a patient.

2. An arrangement as claimed in claim 1, wherein said LCD matrix plate is a black and white liquid crystal display matrix.

3. An arrangement as claimed in claim 1, wherein said LCD matrix plate is a color liquid crystal display matrix.

4. An arrangement as claimed in claim 1, wherein said microprocessor generates control signals for controlling the projection unit based upon said digital pixel image stored in said image memory; an interface unit is provided for converting said control signals from said microprocessor into a form suitable for processing by said LCD matrix plate; and said charge-coupled image sensor receives said distorted image by means of a second fiber optic path within said endoscopic probe.

5. An arrangement as claimed in claim 1, wherein said video monitor is a black and white monitor.

6. An arrangement as claimed in claim 1, wherein said video monitor is a color monitor.

7. An optical three-dimensional measuring probe for the surveying of the three-dimensional geometry of teeth in the oral cavity of a patient, said probe including a highly-resolving two-dimensionally point-by-point freely-programmable projection unit, comprising a projection lamp for generating a plurality of light beams, and an LCD matrix plate, comprising a color liquid crystal display matrix plate, which translates said plurality of light beams into said pixel image for projection onto the tooth surface, an image memory for storing a digitalized projection pattern, an image computer having a microprocessor for the pixel-wise control of said projection unit utilizing a digital pixel image stored in said image memory, said digital pixel image being projected through an endoscopic probe onto the tooth surface which is to be surveyed, a charge-coupled image sensor for converting a distorted image reflected off the tooth surface upon which said digital image is projected into a form suitable for processing by said microprocessor, said microprocessor comprising a program which calculates a topographic representation of the teeth in the oral cavity based upon a comparison between said distorted image and said digital pixel image, and a video monitor for displaying said topographic representation of the teeth in the oral cavity of a patient.

8. An arrangement as claimed in claim 7, wherein said microprocessor generates control signals for controlling the projection unit based upon said digital pixel image stored in said image memory; an interface unit is provided for converting said control signals from said microprocessor into a form suitable for processing by said LCD matrix plate; and said charge-coupled image sensor receives said distorted image by means of a second fiber optic path within said endoscopic probe.

9. An arrangement as claimed in claim 7, wherein said video monitor is a color monitor.

10. A method for the optical three-dimensional surveying of teeth in the oral cavity of a patient with an optical endoscopic probe having a highly resoluting, two-dimensionally point-by-point, freely programmable projection unit comprising an LCD matrix plate, said method comprising the steps of:

controlling, in a pixel-wise manner, said programmable LCD matrix plate to generate at least one image pattern for projection based upon a digital pixel image stored in an image memory;

projecting said image pattern onto the teeth to be surveyed by projecting successive grid patterns of different localized frequency and therefrom there is carried out a rough and fine surveying without ambiguities; and evaluating a reflected image of said projected image for the three-dimensional surveying of particular teeth in the oral cavity of a patient.

11. A method as claimed in claim 10, further comprising the step of projecting a plurality of calibrating markings and surveying patterns into the oral cavity of a patient utilizing said programmable LCD matrix plate.

12. A method as claimed in claim 10, wherein a non-patterned constant light is projected for visual observation and for the automatic recognition of zones of shade.

13. A method as claimed in claim 10, wherein stored reference images and patterns are projected onto the tooth surface which is to be surveyed.

14. A method as claimed in claim 10, wherein images of the oppositely located occlusal surface are projected onto the tooth surface which is to be surveyed.

15. A method as claimed in claim 10, wherein through point-by-point projection there are implemented individual image points of localized height measurements pursuant to a triangulation method.

16. A method for the optical three-dimensional surveying of teeth in the oral cavity of a patient with an optical endoscopic probe having a highly resoluting, two-dimensionally point-by-point, freely programmable projection unit comprising an LCD matrix plate, said method comprising the steps of:

controlling, in a pixel-wise manner, said programmable LCD matrix plate to generate at least one image pattern for projection based upon a digital pixel image stored in an image memory;

projecting said image pattern onto the teeth to be surveyed by projecting colors with a color LCD matrix plate which optimizes the contrast between the tooth surface and the gingiva; and evaluating a reflected image of said projected image for the three-dimensional surveying of particular teeth in the oral cavity of a patient.

17. A method as claimed in claim 16, further comprising the step of projecting a plurality of calibrating markings and surveying patterns into the oral cavity of a patient utilizing said programmable LCD matrix plate.

18. A method as claimed in claim 16, wherein a nonpatterned constant light is projected for visual observation and for the automatic recognition of zones of shade.

19. A method as claimed in claim 16, wherein stored reference images and patterns are projected onto the tooth surface which is to be surveyed.

20. A method as claimed in claim 16, wherein images of the oppositely located occlusal surface are projected onto the tooth surface which is to be surveyed.

21. A method as claimed in claim 16, wherein through point-by-point projection there are implemented individual image points of localized height measurements pursuant to a triangulation method.

* * * * *